(12) United States Patent
Bleuel et al.

(10) Patent No.: US 7,618,828 B2
(45) Date of Patent: Nov. 17, 2009

(54) METHOD FOR HISTOPROCESSING

(75) Inventors: Erik Peter Bleuel, Zuidhorn (NL); Gerard Willem Hofland, Hoogmade (NL)

(73) Assignee: Academisch Ziekenhuis Groningen (NL)

( * ) Notice: Subject to any disclaimer, the term of this patent is extended or adjusted under 35 U.S.C. 154(b) by 480 days.

(21) Appl. No.: 10/562,489

(22) PCT Filed: Jun. 30, 2004

(86) PCT No.: PCT/NL2004/000462

§ 371 (c)(1),
(2), (4) Date: Apr. 5, 2006

(87) PCT Pub. No.: WO2005/001437

PCT Pub. Date: Jan. 6, 2005

(65) Prior Publication Data

US 2006/0228810 A1    Oct. 12, 2006

(30) Foreign Application Priority Data

Jun. 30, 2003    (EP)    ................................. 03077047

(51) Int. Cl.
*G01N 1/00*    (2006.01)
(52) U.S. Cl. .................... 436/174; 435/40.52
(58) Field of Classification Search .............. 436/174; 435/40.52
See application file for complete search history.

(56) References Cited

U.S. PATENT DOCUMENTS 5,993,747 A    11/1999    Mandel (Continued)

FOREIGN PATENT DOCUMENTS

EP    0 822 403    2/1998

(Continued)

OTHER PUBLICATIONS

Mawhinney et al. Control of rapid nitric acid decalcification. J Clin Pathol. vol. 37. pp. 1409-1415. (1984).*

(Continued)

*Primary Examiner*—Jill Warden
*Assistant Examiner*—Jameson Q Ma
(74) *Attorney, Agent, or Firm*—Gerald T. Shekleton; Husch Blackwell Sanders Welsh & Katz

(57) ABSTRACT

The invention relates to the processing of a biological sample for histological analysis. In particular, it relates to a rapid automated processing system that can be operated with continuous throughput and that eliminates the use of toxic solvents such as xylene. Provided is a method for processing a biological sample for histological analysis, comprising contacting the sample with a composition comprising a supercritical or near supercritical fluid followed by impregnating the sample under a pressure of more than 1 bar with an embedding medium, preferably paraffin. Also provided is a processor (1) for preparing at least one sample (10) for histological analysis, comprising at least one process reactor (9) for the at least one sample (10), characterized in that the processor (1) comprises supplying means (4) for supplying to the reactor (9) at least one substance of which at least one is in supercritical phase or near supercritical phase and at least one supplying means (7) for adding the embedding medium to the reactor (9) through conduit (8).

11 Claims, 7 Drawing Sheets

U.S. PATENT DOCUMENTS

Figure 1:
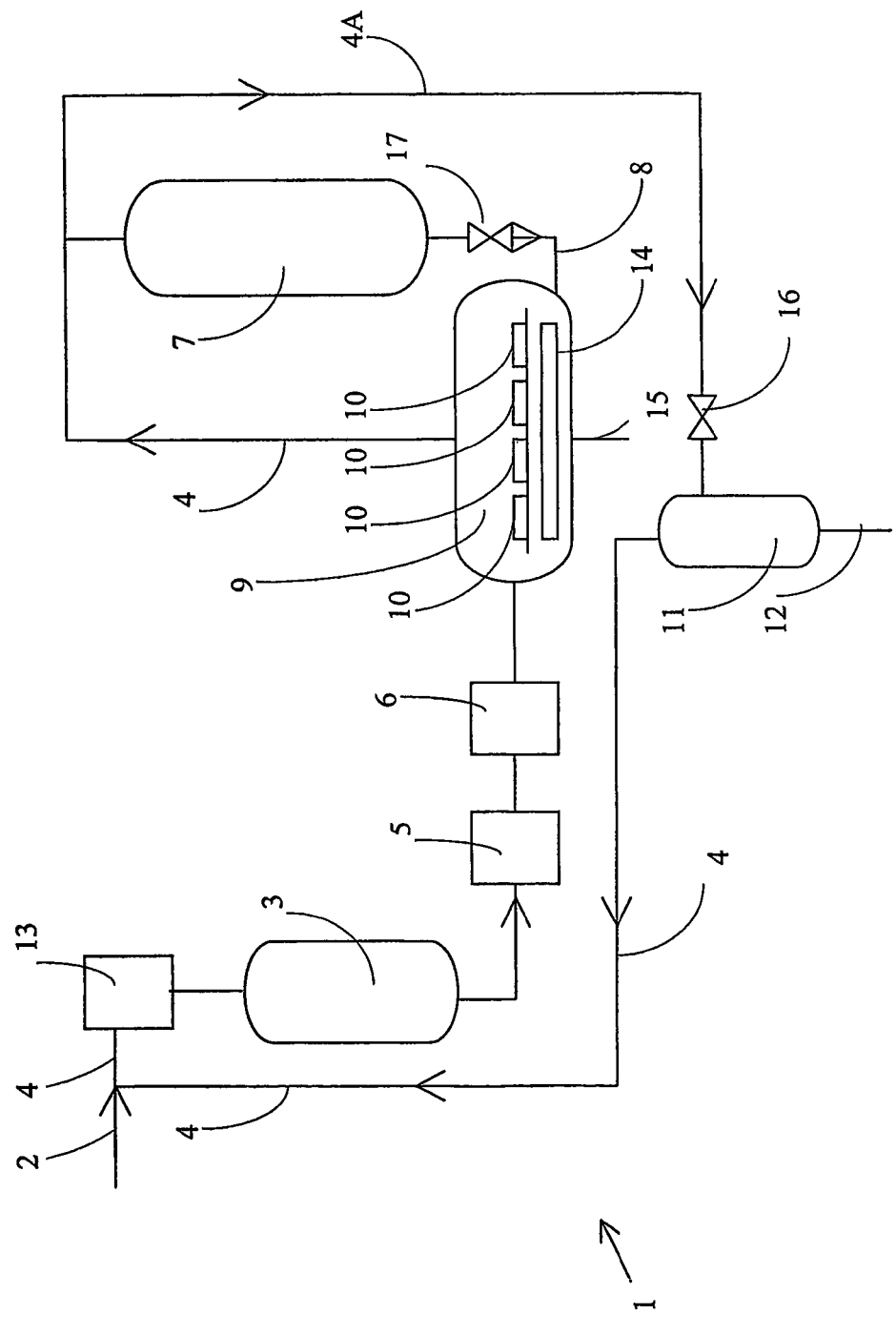

| | | |
|---|---|---|
| 6,493,964 B1 | 12/2002 | Tousimis et al. |
| 2001/0006698 A1* | 7/2001 | Fanta et al. ................. 426/658 |
| 2003/0072677 A1 | 4/2003 | Kafesjian et al. |

FOREIGN PATENT DOCUMENTS

| | | |
|---|---|---|
| WO | WO 00/29037 | 5/2000 |
| WO | WO 01/44783 | 6/2001 |
| WO | WO 01/78911 | 10/2001 |

OTHER PUBLICATIONS

Article entitled "Histological integration of allogeneic cancellous bone tissue treated by supercritical $CO_2$ implanted in sheep bones," (Authors: P. Frayssinet, N. Rouquet, D. Mathon, A. Autefage, J. Fages) (Biomaterials, Elsevier Science Publishers BV., Barking, GB, Biomaterials, vol. 19, No. 24, Dated Dec. 1998, XP004168858, ISSN 0142-9612, pp. 2247-2253, © 1998, Published by Elsevier Science Ltd.).

* cited by examiner

METHOD FOR HISTOPROCESSING

The present invention relates to the processing of a biological sample from fixation to impregnation for histological analysis. In particular, it relates to a rapid and safe automated processing system that can be operated with continuous throughput and that eliminates the use of toxic and (in)flammable solvents such as xylene.

Conventional methods for preparing a sample (e.g. tissue) for histology involve incubation in separate solutions of phosphate-buffered 10% formaldehyde for fixation, incubation in a series of increasing concentrations of alcohol for dehydration, and incubation in xylene for clearing tissue of dehydration agent, prior to impregnation. Because of the time required for this process, usually 8 hours or longer, it is customary to complete these separate steps—fixation, dehydration, clearing, and impregnation-overnight in automated mechanical instruments designed for those tasks (see, for example, U.S. Pat. No. 3,892,197; U.S. Pat. No. 4,141,312; and U.S. Pat. No. 5,049,510).

The ultimate goal of tissue processing is to provide the specimen with internal and external support from a medium of like hardness so that the specimen can withstand microtomy without damage. The most common embedding or support medium is paraffin but many other substances are also used. Microtomy is the process of cutting or sectioning an embedded sample or specimen into thin slices of approximately 2-8 microns in thickness with a sharp steel knife in a microtome. Slices are then picked up on slides, usually microscope slides.

Standard paraffin processing procedures include exposure to chemical dehydration through graded alcohol solutions, then immersion in a transition solution (commonly referred to as a clearant) followed by impregnation with paraffin. Dehydration means the removal of water. During processing procedures, dehydration is used to remove the free water molecules and, if performed correctly, also the molecularly bound water. Dehydration is normally accomplished using alcohol solutions; most commonly ethanol, isopropylalcohol (isopropanol); occasionally methanol; or butanol for plant and animal tissue. If specimens are improperly dehydrated and water is left in the specimen, the clearant and impregnation agent (for example paraffin) will not penetrate the tissue and it will be soft and mushy. Excessive dehydration will remove the bound water, causing shrunken, hard, brittle specimens that require excessive rehydration before sectioning.

Fat in a tissue sample is removed with a solvent because fat impairs clearing and impregnation. Inadequate fat removal (defatting) can result in spreading artefacts of tissue sections, wrinkling of tissue sections, and poor staining. Fat may be removed from the tissue specimen with various solvents such as, for example, acetone, chloroform or xylene.

Following dehydration of a sample, a "clearing" agent is used to remove alcohol used for dehydration from the sample and to prepare the sample or specimen for the impregnation medium. Clearing agents, also referred to as "dealcoholization" agents, must be miscible with both the dehydrating agent and the impregnation/embedding medium. Inadequate clearing, which can be caused by water remaining in the specimen or by inadequate exposure times, causes poor paraffin infiltration which will result in soft, mushy specimens. On the other hand, excessive exposure to clearing agents will produce hard, brittle specimens caused by the denaturation of the tissue proteins that is very similar to the effect of excessive dehydration.

Xylene (dimethylbenzene) has been the most widely used clearant for many years. It is an aromatic hydrocarbon that rapidly replaces alcohol and has a refractive index capable of rendering the tissue transparent. A major drawback of xylene is that it is very cumbersome to use, because it is highly volatile, flammable and a suspected carcinogen. Xylene should therefore only be used with adequate ventilation, and skin contact should be avoided. In addition, xylene is expensive.

Effective replacements for xylene have been actively sought for. A first substitute that was presented in 1981 was limonene. Unfortunately, that chemical has cast a shadow over the subject because of several issues. Limonene is oily and cannot be recycled reliably (the recycled solution is different from the original product). Its odour is overpowering and quickly pervades neighbouring rooms and halls. Most troublesome is the fact that it causes serious sensitization reactions in exposed workers. Other xylene substitutes are short chain aliphatic hydrocarbons (alkanes). Essential oils can also be used as xylene substitute but they are not as common. However, none of these xylene substitutes has proven as useful and cost-effective as xylene.

Conventional procedures for tissue processing can be performed both manually or in an automated fashion. Most histopathology labs now use automated tissue processing machines which use multiple containers and require 6-20 hours for processing. Automated tissue processors implementing such conventional processes are manufactured and sold by, for example, Shandon (HYPERCENTER and PATHCENTRE models), Miles-Sakura (TISSUE-TEK models), and Mopec-Medite (TPC15 model).

A disadvantage of the systems of the prior art is that such automated systems have not been capable of continuous throughput. Given the time required to complete tissue processing, cassettes containing tissues are loaded into the system during the day and tissue processing is completed in an overnight cycle. Thus, operation of the prior art systems did not allow tissue-containing cassettes to be processed to completion during the work day.

Typically such conventional methodology demands sending tissue specimens from the operating room, medical office or other sites, to a pathology laboratory sometime during the working day, followed by overnight batch processing of the specimens, so that a tissue specimen suitable for blocking and sectioning is at the earliest only available on the morning of the next day; and rendering a diagnosis by a pathologist based on microscopic examination of sections prepared from a blocked and sectioned specimen is only possible later on that next day. This minimally requires almost 24 hours between receipt of the specimen and delivery of the pathologist's report.

In addition to the minimum one-day delay in giving a medical practitioner (e.g. a surgeon) the benefit of a report from the pathologist, there are also problems associated with impeded work flow in the pathology laboratory necessitated by the requisite batch processing of specimens, the safety concerns that attend having instruments operating overnight, the risk of possible instrument failures and the need to monitor the instruments, and the waste of using large volumes of reagents for such processing when automated. Moreover, expensive measures are required to prevent exposure of laboratory personnel to noxious fumes and toxic substances associated with the reagents (such as xylene) used in this process. Also, the large volumes of solvent waste and paraffin debris produced by the conventional methodology will pollute the environment if not properly disposed.

There is an ever present interest in expediting tissue processing and analysis for diagnostic purposes. Furthermore, recent healthcare focus has been directed to lessening the cost of various procedures including tissue processing. The costs of tissue processing are related to the time for processing and analysis of the specimens, the space required for the personnel and equipment in the laboratory, the volume of reagents (both the purchase price of the pure chemicals and the charges for discarding waste), and the number of personnel required. More importantly, patients and their physicians depend on evaluation and diagnosis by the pathologist to guide treatment. Reducing the amount of time needed to complete tissue processing would lessen the anxiety experienced during the period between obtaining the specimen and delivering the pathologist's report to the physician. Thus, a significant reduction in the time required for processing of a histological sample is very desirable. Others have also recognized the need to shorten the time required for tissue processing, but they have made only modest improvements in the conventional methods. To accelerate tissue processing, U.S. Pat. Nos. 4,656,047, 4,839,194, and 5,244,787 use microwave energy; U.S. Pat. Nos. 3,961,097 and 5,089,288 use ultrasonic energy; and U.S. Pat. No. 5,023,187 uses infrared energy. U.S. Pat. No. 5,104,640 disclosed a non-aqueous composition of a fixative, a stabilizing agent, and a solubilizing agent that adheres a blood smear to a slide.

The inventors now describe a method for tissue processing in a manner distinct from any of the procedures currently used. Provided is a method for processing a biological sample for histological (or pathological) analysis, comprising contacting the sample with a composition comprising a supercritical or a near supercritical fluid followed by impregnating the sample with an embedding medium under a pressure of more than 1 bar.

A method in accordance with the present invention is faster than any of the reported methods, causes minimal damage to the processed tissue, avoids the use of organic solvents including xylene, uses minimal amounts of reagents, and, surprisingly, results in a superior specimen for subsequent cytological, histological or anatomical analysis. In addition, with a method according to the invention it is no longer necessary to use large (plastic) containers with an inflammable liquid such as ethanol or xylene.

A supercritical fluid, sometimes called a supercritical gas fluid or a fluidum, is any substance above its supercritical temperature ($T_c$) and its supercritical pressure ($P_c$). For every substance, there is a temperature above which it can no longer exist as a liquid, no matter how much pressure is applied. Likewise, there is a pressure above which the substance can no longer exist as a gas no matter how high the temperature is raised. This point is called the supercritical point; the critical temperature and critical pressure are the defining boundaries on a phase diagram for a pure substance.

In the supercritical area there is only one state-of-the-fluid. A supercritical fluid exhibits physicochemical properties intermediate between those of liquids and gases. Supercritical fluids (also known as highly condensed gases) are able to spread out along a surface more easily than a true liquid because they have lower surface tensions than liquids. At the same time, a supercritical fluid maintains a liquid's ability to dissolve substances that are soluble in the compounds, which a gas cannot do.

According to the invention, a (tissue) sample is contacted with or surrounded by a supercritical fluid, comprising pressurizing the sample with the composition comprising a (near) supercritical fluid to above the critical pressure ($P_c$) of the supercritical fluid and heating the sample with the supercritical fluid to above the critical temperature ($T_c$) of the supercritical fluid. The supercritical fluid penetrates a sample as it passes by a sample in a high-pressure vessel. It may not always be necessary to use a substance that is at or above its supercritical point (i.e. above its $T_c$ and $P_c$), as long as the properties (especially the solubilizing capacity) of the substance are of use in a method for histoprocessing. For example, a near supercritical fluid, which is at a pressure and temperature in the vicinity of the supercritical point can also be advantageously used in a method provided herein. According to the invention, the term "near supercritical fluid" is defined as a fluid at a temperature in the range of about 0.7 to about 1.4 times its $T_c$ and at a pressure in the range of about 0.3 to about 7 times its $P_c$.

In a preferred embodiment, a sample is contacted with a composition comprising (near) supercritical carbon dioxide ($CO_2$). The supercritical pressure of $CO_2$ is about 7.3 MPa (73 bar) and the supercritical temperature is approximately 31° Celsius. Biological tissues contain proteins which denature by temperature above approximately 60° C. The relatively low supercritical temperature of $CO_2$ allows to contact a sample with a supercritical fluid at a temperature that has essentially no detrimental effects on the biological sample. However, other (near) supercritical fluids with a relatively low supercritical temperature (preferably lower than 60° C.) are also suitable for use in a method according to the invention, for example xenon, nitrous oxide, ethane, HFC-116, chlorotrifluormethane, ethylene, sulfur hexafluoride and trifluormethane. $CO_2$ is extremely attractive in industrial applications because it is the second most abundant and the second least expensive solvent on earth. It is non-flammable, non-toxic, readily available in high purity.

An embedding or supporting medium provides the sample with mechanical support such that sections can be prepared, e.g. for microscopical examination. A preferred embedding medium according to the invention is a liquid embedding medium, for example liquid paraffin. Paraffin has been chosen as embedding medium in the examples herein because it is soluble in supercritical $CO_2$ (or, vice versa, $CO_2$ is soluble in paraffin) inexpensive, easy to handle, and ribbon sectioning is facilitated by the coherence of structures provided by this material. Other suitable embedding or impregnation materials are commercial wax formulae, mixtures of waxes of different melting points (e.g., liquid mineral oil and solid paraffin), paraplast, bioloid, embedol, plastics, and the like.

According to the invention, a sample is typically first immersed into ethanol or other type of dehydrating agent in order to replace water in the sample. The sample is then pressurized with a (near) supercritical fluid to remove the dehydrating agent such as ethanol. At (near) supercritical conditions, the dehydrating agent and the fluid are miscible i.e. they dissolve completely in each other whatever the proportions of the components is. Subsequently, the (near) supercritical fluid is replaced by infiltrating an embedding medium while maintaining an elevated pressure i.e. a pressure above the pressure of 1 bar (1 atmosphere, 1 kg/cm²). The (near) supercritical fluid within the sample is dissolved in the embedding medium while at the same time it is being gradually replaced by the paraffin. The elevated pressure during the infiltration step ensures that no gas is trapped in the tissue and that the cellular structures remain preserved. Preferably, the pressure applied is at least 50 bar, more preferably at least 100 bar, such as 120 or 150 bar or even higher, such as around 200 bar. Generally speaking, the higher the pressure applied, the higher the solubility of the (near) supercritical fluid in the embedding medium and the more efficient the fluid will be replaced by the embedding medium. For example, it has been observed that the solubility of $CO_2$ in liquid paraffin is approximately 15% by weight at 80 bar at 55° C., approximately 30% (w/w) at 120 bar and around 50% at 180 bar. The temperature at which impregnation according to the invention can be performed can vary and depends among others on the embedding medium used. Typically, a temperature above the melting point of the embedding medium is chosen. In case of paraffin, this is a temperature of 56-58° C. However, under elevated pressure the melting point is usually reduced. For example, at a pressure of 110 bar paraffin starts to melt at 51° C. and is completely melted at 57° C. When increasing the temperature of a reactor comprising a sample (see FIG. 1) above the melting temperature, the pressure in the reactor is increased. In one embodiment of the invention, a sample is contacted with $CO_2$ at a pressure of 150 bar at around 40° C. during 0.5-1 hour to remove ethanol from the sample. Subsequently, the sample is heated to 65° C. while maintaining the density of $CO_2$ such that the pressure increases to around 220-250 bar. Liquid paraffin is allowed to enter the reactor, while $CO_2$ is allowed to leave the reactor while trying to maintain a constant pressure. The reactor is completely filled with paraffin over a time period of about 30 minutes to remove and/or dissolve $CO_2$ from the sample. During this stage of the process, the pressure may drop, e.g. to 100-140 bar. Once the sample is fully immersed in the paraffin, the pressure can be gradually decreased to allow diffusion of $CO_2$ from the tissue into the paraffin and to avoid that $CO_2$ bubbles become trapped in the tissue.

After the sample is depressurized, it may be advantageous to leave the samples for some period of time (e.g. 10-60 minutes) in the warm paraffin.

The phenomena of enhanced solubilities in supercritical fluids has been known since the late 1800s. For decades they have been used in food processing industries to extract flavouring compounds such as caffeine and hop oil. The solubilizing power of supercritical fluids is sensitive to small changes in the operating conditions, and it is possible to fine-tune the pressure and the temperature to tailor the solvent capacity of a supercritical fluid for a particular process. The desirable and unique properties of supercritical fluids have provided the impetus for applying supercritical fluid technology to various other problems, e.g. the cleaning of fabrics or the sanitization of contaminated soil.

Supercritical fluid extraction has been used in methods for preparing sterilized tissue for incorporation into xenografts and bioprostethic devices. US Pat. Appl. No. US2003/0072677 describes the use of supercritical fluids to remove infectious materials from tissues and to treat the tissue with a chemical agent. Unlike the present invention, US2003/0072677 does not relate to processing samples for further examination, let alone to the application of supercritical fluids in histological (embedding) procedures. U.S. Pat. No. 6,493,964 discloses a supercritical point drying apparatus for sample preparation in electron microscopy and semiconductor wafer production. It utilizes the technique of substituting a supercritical 'transitional' fluid for the dehydrating fluid in the cell structure and then removing the transitional fluid. However, U.S. Pat. No. 6,493,964 does not relate to sample impregnation and doe not teach or suggest that supercritical fluids are advantageously used as intermediate between dehydration agents and an embedding medium while maintaining an elevated pressure, that such use results in a superior quality of the specimen (see below) compared to conventional procedures. EP0822403 relates to processing of organic tissues to prepare them for further investigation using an inert gas at increased pressure, such that the sample can be treated at higher temperatures. The pressure may be built up by introducing an inert gas in the container comprising the tissue sample, for example $CO_2$. It is mentioned that a dehydration/clearing step is preferably carried out simultaneously at a pressure up to 10 bar and at a temperature from room temperature to up to 90° C. Under these conditions, $CO_2$ is not in a supercritical or near supercritical state. Thus, the process of EP0822403 entails an entirely different concept compared to a method of the invention and does not involve a (near) supercritical fluid. Moreover, EP0822403 mentions that impregnation is preferably carried out under vacuum.

In a method for histological processing according to the invention, a sample is treated with a (near) supercritical fluid and subsequently impregnated with an embedding medium under elevated pressure. In one embodiment, a method of the invention further comprises dehydration, defatting and/or decalcification of said sample prior to impregnation. Said additional processing step(s) may be performed using the conventional procedures mentioned above. Preferably however, they are performed making use of a supercritical fluid. In one embodiment, a method is provided for processing a sample wherein said processing comprises dehydration of said sample using a supercritical fluid. For example, a sample is contacted with a supercritical fluid to solubilize and remove water from said sample prior to impregnating the sample with an embedding medium. A supercritical fluid can be mixed with an other solvent, to aid in extracting certain substances (e.g. water) from a sample. In one embodiment, a sample is dehydrated with a composition comprising a supercritical fluid and a dehydrating agent, preferably an alcohol, such as ethylalcohol (ethanol; EtOH) or a detergent, such as Tween. Dehydration using a supercritical fluid as provided herein is typically accomplished fast, sometimes even within minutes. Thus, the invention combines the improved embedding procedure with an attractive alternative for the time-consuming traditional step-wise dehydration using graded alcohol solutions. Advantageously, the supercritical fluid dissolves and extracts other substances from a sample, such as fats and lipids, thereby facilitating cutting a sample into thin slices. In a specific embodiment, processing of a sample, in particular a calcified tissue like a bone specimen, comprises removing calcium from a sample. Decalcification of a sample is important for cutting thin slices from bone tissues and other calcified particle in tissues, because calcified structures are in general difficult to cut. Traditional decalcifying protocols require the additional incubation of a fixed sample during one to five nights in an acidic decalcifying solution (typically formic acid, acetic acid, hydrochloric acid or nitric acid). Decalcification is also performed using a calcium-chelator such as EDTA (ethylenediaminetetra acetic acid). According to the invention, decalcification of a sample is accomplished simpler and faster when compared to existing decalcification methods. Hereto, a biological sample is contacted with a composition comprising a (near) supercritical fluid, wherein said composition additionally comprises a decalcifying agent. Suitable decalcifying agents include acids such as carboxylic acids, for instance formic acid or acetic acid, and other chemicals capable of binding or sequestering calcium.

When a composition comprising a supercritical fluid and additionally comprising a co-solvent (e.g. for water and/or calcium) is used, the supercritical fluid and the co-solvent (e.g. an alcohol and/or an acid) can be supplied as a mixture in a cylinder. Another method of supplying the additional co-solvent can be achieved by using an additional pump systems onsite to mix the required co-solvent to the supercritical fluid.

Histological analysis as used herein refers to any type of analysis that may be performed to study the appearance, properties and behaviour of a tissue, a cell, an organ or an organism. It can be carried out by inspecting a processed sample under a microscope. A (component of a) processed sample can be contacted with one or more reagents, such as a dye, a reagent or a probe specifically reactive with one or more components (such as proteins, nucleic acids, carbohydrates) present in the sample to identify or mark a certain cell type or tissue. A tissue refers to a group or layer of cells which are essentially alike and work together to perform a specific function. Typical probes include antibodies (e.g. for immunohistochemistry), nucleic acid (RNA; DNA) probes (e.g. for in situ hybridisation or PCR techniques), substrates for use in enzyme histochemistry (e.g. NADH for detecting acetyl cholinesterase or ATP-ase activity) and conventional staining chemicals such as hematoxylin and eosin (H&E); Alcian Blue for sulfated mucosubstances; Brown-Brenn Gram stain for Gram-positive and Gram-negative bacteria; Congo Red for amyloid; Giemsa for *H. pylori*; and Bone Marrow; Gomori's Modified Iron stain; and many other probes known to a person skilled in the art that are of use to identify or mark a certain cell type or tissue, be it normal or diseased.

Pathological analysis refers to histological analysis that is related to pathology. Typically, pathological analysis is performed by a pathologist who diagnoses disease by studying a sample comprising cells and tissues under a microscope. In a preferred embodiment, a pathological analysis comprises analysis of a human sample to stage or grade a disease.

According to the invention, a sample comprises a biological sample, such as a tissue specimen. In the context of the invention, a "tissue specimen" is any piece of tissue that may be processed by a method disclosed herein. It may also refer to single cells from any biological fluid (e.g., ascites, blood, pleural exudate), or a cell suspension obtained from aspiration of solid organs or lavage of body cavities. Single cells may be pelleted by sedimentation or buoyant centrifugation prior to processing. It may also refer to an intact organ, or even an intact organism, or a part thereof. Organisms include unicellular and multicellular organisms, and range from bacteria, fungi, insects and plants to mammals. Solid pieces (i.e., tissue slices or needle biopsies) from a human subject are commonly processed for histology and pathology. Where conventional methods for the fixation and embedding of an organ (e.g. brain) require up to 6-8 weeks, a method of the invention now allows impregnation of an (intact) organ or a part thereof with a solid embedding medium within a day and without the use of toxic (clearant) solvents.

With a method of the invention, it is possible to reduce total processing time (from fixation to impregnation) from the conventional 8-12 hours to less than 2 hours, preferably less than 1.5 hours, more preferred less than one hour. Nowhere in the prior art it has been taught or suggested that the entire process of preparing diagnostic tissue slides could be accomplished in less than 1.5-2 hours, starting from the preparation of a specimen from a fixed or non-fixed tissue and ending with impregnation, with continuous processing of specimens, circumventing the use of toxic, possibly carcinogenic clearants and a superior quality of the sample. WO 01/44783 discloses a tissue processor system including an improved microwave unit that allows rapid processing under two hours and, optionally, without the use of xylene clearants. However, the protocol of WO 01/44783 can only process a tissue specimen with a thickness of less than about three millimetres. In contrast, in a method of the present invention, samples up with a thickness to 5 millimeters, such as 8 mm or even more than 1 centimeter may be rapidly processed using a supercritical fluid. As mentioned above, and unlike WO 01/44783, a method of the invention is not limited to tissue samples or small tissue sections. A method according to the invention allows to process a sample with a volume ranging from about 0.001 cm$^3$ (e.g. a biopsy) or 1 cm$^3$ (e.g. a skin specimen) up to 10 cm$^3$ (e.g. a small tumor) or even up to larger samples such as those with a volume of 2000 cm$^3$ (e.g. an organ such as complete brains). In general, according to a method of the invention, the larger the sample, the more time it will take to process the sample. However, in comparison with the prior art the time gain achieved with the present invention also increases with the size of the specimen. For example, a tissue specimen of 20×15×5 mm is rapidly dehydrated and impregnated according to a method of the invention. This offers a considerable advantage, in that a sample can be processed of such a volume or size that it is possible to obtain multiple (microtome) slices from said sample. For instance, following histological inspection of a sample, a pathologist may want to inspect the same sample that has been stained with a specific reagent, such as an antibody, to aid in the histological analysis. Processing a sample according to the invention allows to simply provide a second, third or even higher number of (parallel) slices from the same sample. If the specimen is already less than 3 millimeter before processing, as is the case in WO 01/44783, this is obviously not possible. Instead, multiple samples need to be taken at the outset and their relative orientation needs to be carefully registered to reconstruct their connection in situ.

Figure 2:
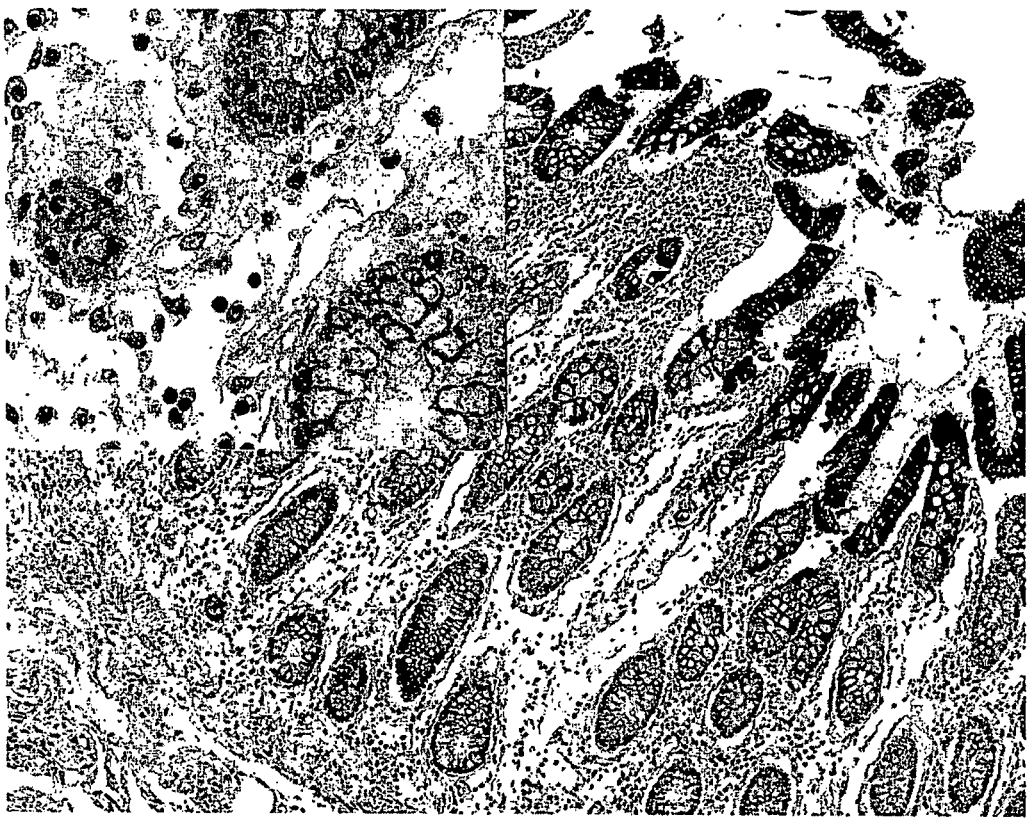
Figure 3:
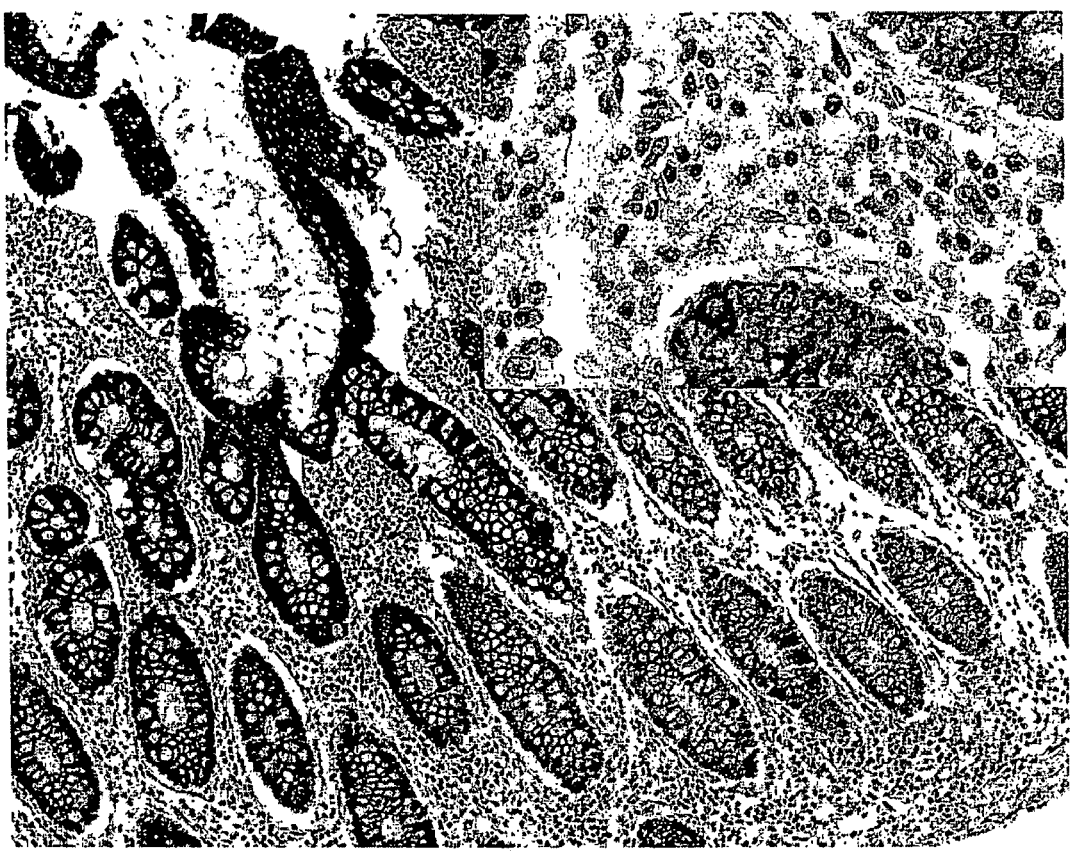

Histological analysis of various types of human tissue specimens that were processed using a supercritical fluid according to the invention surprisingly revealed a superior quality of the specimen compared to specimens from the same tissue sample that were processed according to conventional procedures. For example, the keratin staining pattern of a human colon specimen following processing using carbon dioxide shown in FIG. 3 is more intense compared to the keratin staining pattern of FIG. 2, showing a specimen from the same colon sample which was processed using conventional methods. Likewise, improved histological analysis could be performed on a vimentin-stained human gall bladder specimen processed according to a method of the invention (compare FIGS. 3 and 4) and on a human nerve specimen stained for S-100 protein (compare FIGS. 6 and 7).

In one embodiment of the invention, a sample is fixed according to conventional methods prior to being processed according to a method according to the invention, for instance using a formaldehyde solution (also known as formalin). Formaldehyde ($CH_2O$) reacts with terminal free $—NH_2$ groups of proteins and forms covalent methylene bridges between two components of a protein or between two different proteins. However, a major drawback of conventional fixation and tissue processing (i.e. into paraffin blocks) lies in the fact that it can cause irreversible damage (e.g., hydrolysis of a phosphodiester bond and/or deamidation) to the structure of nucleic acids (e.g., DNA, and especially RNA). Accordingly, fixing and processing of a (tissue) sample into a paraffin blocks limits the application of genetic techniques for diagnosis and research.

In one embodiment of the present invention, a sample that has been previously frozen is processed according to a method of the invention. It is known in the field that most DNA and certainly RNA analyses require special precautions with handling of sample material, such as immediate ("snap") freezing of fresh tissues into liquid nitrogen to prevent nucleic acid degradation. A method of the present invention can be used for impregnating a (snap) frozen sample and the invention thus provides a method for obtaining a processed biological sample that can subsequently be analysed for various types of histological analysis, including nucleic acid (DNA, RNA) analysis. On the other hand however, histological diagnosis of a frozen section may suffer from disadvantages in comparison to sections prepared from paraffin blocks. For instance, frozen sample are prone to dehydration. Storage of frozen samples therefore requires measures to prevent dehydration. Importantly, frozen tissues often show many artefacts that are caused by the presence of ice crystals in the sample. Thus, it may sometimes be difficult to adequately weigh the advantages and disadvantages that are associated with either a fixed or frozen samples against each other.

A method in accordance with the invention for processing a sample now provides an elegant solution to these problems, because in addition to processing a fixed or frozen sample, it also allows for rapid processing a fresh sample that has not been fixed or frozen prior to being contacted with a supercritical fluid. Instead of freezing or using a chemical fixative, the high pressure encountered by the sample during contacting with a supercritical fluid and the rapid impregnation with an embedding medium (e.g. paraffin wax) under elevated pressure ensures an optimal preservation of the structure and architecture. Surprisingly, no damage to the tissue sample occurs if pressure is increased and subsequently gradually decreased. Pressurizing the tissue can be performed relatively fast. The cells within the tissue are filled with liquid which will withstand a rapid pressure increase. However, the sample should be gradually depressurised to avoid rapid expansion of the fluid and rupture of the cells. Thus, the invention provides an attractive alternative for snap freezing a sample and allows for preparing a sample that is compatible with multiple types of (pathological) analysis including histological, biochemical and nucleic acid analysis, without the use of formalin.

Importantly, in addition to the reduction in time required for tissue processing, the rapid tissue preparation using a supercritical fluid allows for preserving tissue structures and morphology that are lost with conventional methodology. Glycogen, which is an important compound giving strength to biological structures, is almost always lost using the conventional methodology. Lymphatic vessels, particularly of the myometrium, collapse during conventional processing while they remain essentially intact when a method of the present invention is used. Moreover, studies with tissues processed in accordance with the invention indicate better preservation of DNA and RNA extraction as compared to conventional processing methods. Tissues obtained in hospitals and other surgical settings can be processed for both histological and genetic studies soon after delivery to the laboratory. In addition, because a sample processed in accordance with the invention is typically well preserved, archival sample material may be made available for future research and other applications.

The present invention does not prohibit preparation of nucleic acids, DNA or RNA, from processed samples. Thus, genetic study is possible for specimens collected routinely in the clinical pathology laboratory. The combined power of these technologies will be great. Histological observations may be correlated with results from genetic studies by analyzing one histochemical section by staining or immunohistochemistry, and analyzing nucleic acids from an adjacent section for genetic analysis (using for example PCR techniques). For example, diseased and normal regions of the same section may be compared to detect genetic differences (e.g., mutations, levels of transcription), disease progression may be characterized by comparing genetic differences in samples taken at several time points, and tumor evolution may be assessed by following the accumulation of genetic differences from primary cancer to metastasis.

A further advantage of a method according to the invention relates to sample or specimen orientation. Specimen orientation is key to reach the end result—the correct diagnosis. In existing procedures, a processed (embedded) specimen is placed in a specimen holder or mold to enable sectioning of the tissue in a microtome. Fixation and immobilization of a sample, frequently small and delicate, in the correct orientation into a holder is often troublesome. Because most glues are not compatible with the organic solvents used in histo-processing, molds with a roughened or "sticky" surface are typically used to attach a specimen to the bottom of a mold or holder. However, these holders often do not sufficiently fix a specimen such that it can be sectioned. Other specimen holders are provided with snap-on lids to immobilize a sample by simply clamping a sample in between the bottom and the lid. Still, these holders are not suitable for delicate specimens such as skin or epithelial tissues because the pressure required to clamp a specimen easily disrupts the integrity of such tissues, e.g. evidenced by collapsed blood vessels. The invention now provides a solution to these problems. Since a method of the invention does no longer require organic solvents (xylenes) which previously disqualified the use of glues, a specimen can now simply be glued in a desired orientation to the bottom of a holder. Moreover, as mentioned earlier, a method of the invention is suitably used to impregnate samples of considerably larger size than could be used thus far. As a consequence, it is now even possible to first orient an intact tissue, organ or even organism, prior to processing. For example, a tumour is removed in the operating theatre. Instead of cutting the tumour into multiple small size specimens, thereby carefully keeping track of their relative orientation, the invention now permits to orient and embed the whole, intact tumour.

We have developed a simple, safe, low cost, expeditious, and reliable process that permits preparation of impregnated tissue blocks suitable for microtome sectioning in less than 1.5 hours from the moment tissue is received in the pathology laboratory. The invention allows continuous processing and flow of specimens, either fresh, fixed or frozen, is adaptable to automation, precludes the need for formalin and xylene with their noxious fumes, allows standardization of tissue processing, and requires considerably smaller volumes of reagents than conventional methods. By "continuous" processing, we mean accessing the system of the invention with additional tissue specimens at intervals determined by the time required to complete an individual step of the process (i.e., a few minutes) instead of the time required to complete the process (i.e., an hour to several hours). At any given time, there can be samples at different stages of processing. In other words, a continuous throughput and flow of specimens along the various stages of tissue processing is made possible by the invention. Continuous processing may be accomplished manually or by an automated instrument, such as a tissue processor.

In one aspect of the invention, a processor is provided for use in a method of the invention. An embodiment of such a processor according to the present invention will now be described by way of example with reference to FIG. 1 in the accompanying drawing.

FIG. 1 schematically shows an example of a processor according to the invention.

The processor 1 of FIG. 1 comprises a storage tank 3 and a conduit system 4. The conduit system 4 has an inlet 2 for supplying to the processor a substance, in this example assumed to be liquid carbon dioxide. The carbon dioxide is transported through a conduit of the conduit system 4 through a cooler 13 into the storage tank 3. The processor 1 comprises downstream of the storage tank 3 pressurizing means 5 and heating means 6, both for bringing the carbon dioxide at the required conditions. The carbon dioxide is supplied to a process reactor 9. This reactor 9 may contain samples 10 to be prepared by the processor 1 for histological analysis. The reactor 9 comprises heating and/or cooling means 14 for maintaining the carbon dioxide in the reactor 9 at the required conditions. With these conditioning means 14 of the reactor 9 the different steps of the different methods of the invention as described above can be performed in the process reactor 9. Downstream of the process reactor 9 the processor 1 further comprises a pressure control valve 16, subsequently followed by separation means 11 for separating different substances from the mixture of substances leaving the reactor 9. The extracted substances such as alcohol, paraffin, water, etcetera, can leave the extraction means through outlets 12. Some of these substances, for example paraffin, can be re-used. The carbon dioxide left over from the mixture can be recycled. To that end, it is fed from the separation means 11 via conduit 4 into a recycling means 13, for example a carbon dioxide gas cooler 13 comprised in the conduit system 4 of the processor 1, after which the liquefied carbon dioxide is fed to the storage tank 3 again. When the reactor 9 is sufficiently flushed with carbon dioxide, pump 5 is stopped and the pressure vessel 7 containing the embedding medium (e.g. paraffin) is emptied into reactor 9 by opening valve 17, such that the embedding agent flows on gravity through conduit 8 and flows into reactor 9. Pressure vessel 7 is kept under pressure because it is connected to the conduit 4. Here the samples 10 are impregnated with the embedding medium, where after the reactor 9 and pressure vessel 9 can subsequently depressurised through conduit 4A into separation vessel 11 and emptied through outlet 15.

Having described an example of a processor 1 according to the invention, many modifications thereto will become apparent to those skilled in the art without deviation from the invention as defined by the scope of the appended claims. For example, it is possible to apply in a single processor a larger number of reactors, pressure vessels, storage tanks, pumps, control means, valves, etcetera. The pumps for instance may be used to add co-solvents or dehydration agents (e.g. ethanol, acetone, formaldehyde, etcetera).

EXAMPLE

Human gall bladder, colon, and nerve specimens impregnated with ethanol were placed in a 1 litre reactor. The reactor was maintained at a temperature of 40° C. The reactor was closed and pressurized to 150 bar with carbon dioxide at 40° C. While maintaining the pressure at 150 bar applying a control valve, the reactor was flushed with fresh carbon dioxide at a rate of 10 kg/h applying a pump. After 45 minutes, the pump was stopped and the temperature was raised to 60° C. Raising the pressure to approximately 230 bar. Molten paraffin of 60° C. was slowly pumped into the reactor at a rate of 2 litre/h, impregnating the specimen, while maintaining a pressure of 210 bar. After the reactor was nearly completely filled with paraffin, the reactor was depressurized in 10 minutes. Excess paraffin was drained from the reactor and the reactor was cooled to 40° C., after which the embedded specimens were collected from the reactor. The specimens were histologically analysed according to conventional procedures.

LEGENDS

FIG. 1
Example of a processor according to the invention.

FIG. 2
Human colon specimen (100×; insert 400×) processed according to the conventional high throughput Sakura VIP-300 bench-top automated tissue processor. Keratine was stained using Keratine 20 (monoclonal Mouse Anti Human Cytokeratin 20 Clone KS 20.8 clone no M7019 lot 067 from Dako). A Ventana NexES™ automated immunostainer was used.
Specificity: epithelial cells of the mucosa of the large intestine are stained, no background staining visible.
Intensity: diffuse staining pattern along the entire crypt.

FIG. 3
Human Colon specimen (100×; insert 400×) from the same sample as shown in FIG. 2 but processed using super critical carbon dioxide. Staining was performed as described for FIG. 2.
Specificity: epithelial cells in the mucosa of the large intestine are stained, no background staining visible.
Intensity: diffuse staining along the entire crypt, staining is enhanced compared with the conventional method (VIP).

Figure 4:

FIG. 4
Human gall bladder specimen (100×; insert 400×) processed by standard procedure VIP300.
Vimentin was stained using an anti-vimentin antibody (clone vim 3B4) cat nr 112457 Boehringer Mannheim) and the Ventana staining according to protocol.
Specificity: mesenchymal cells in the lamina propria and the deeper layers of the gallbladder are stained. Epithelial cells are negative.
Intensity: diffuse intracytoplasmatic staining of the mesenchymal cells.

Figure 5:
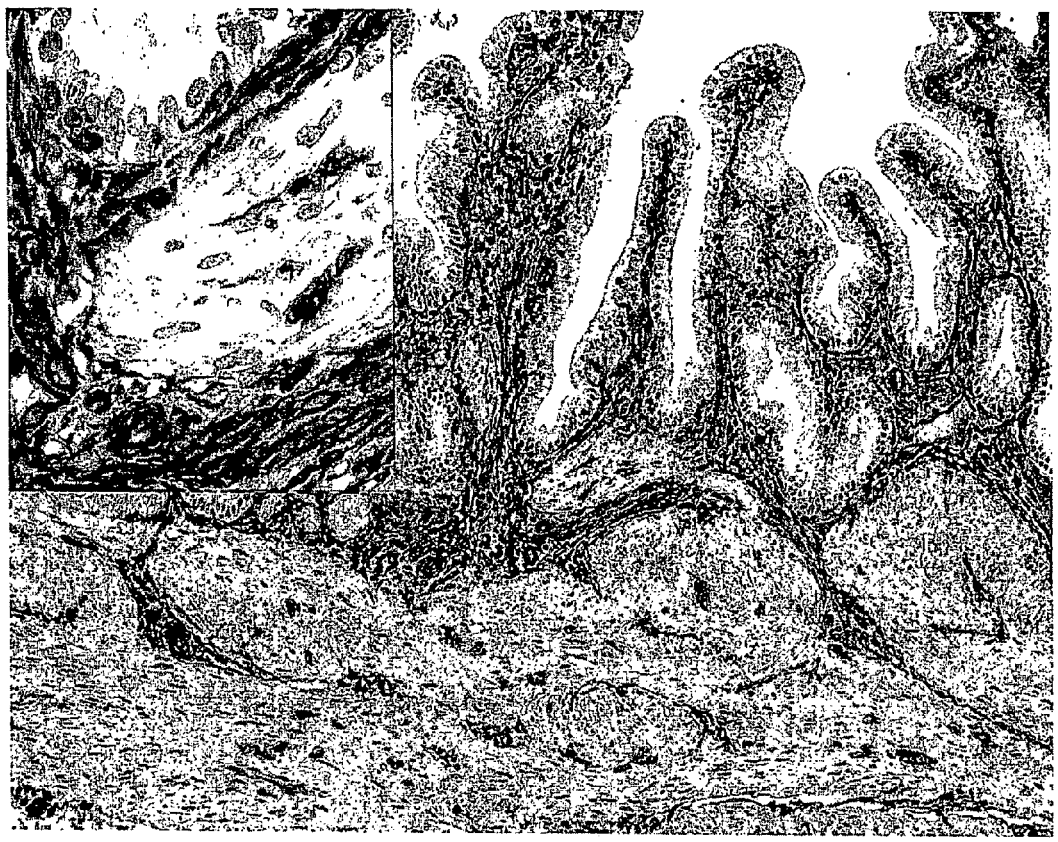

FIG. 5
Human gall bladder specimen (100×; insert 400×) of the same sample as shown in FIG. 4 but processed using supercritical carbon dioxide.
Staining was performed as described for FIG. 4.
Specificity: mesenchymal cells are stained in the lamina propria and deeper layers of the gall bladder.
Intensity: enhanced compared with the conventional procedure (VIP).

Figure 6:
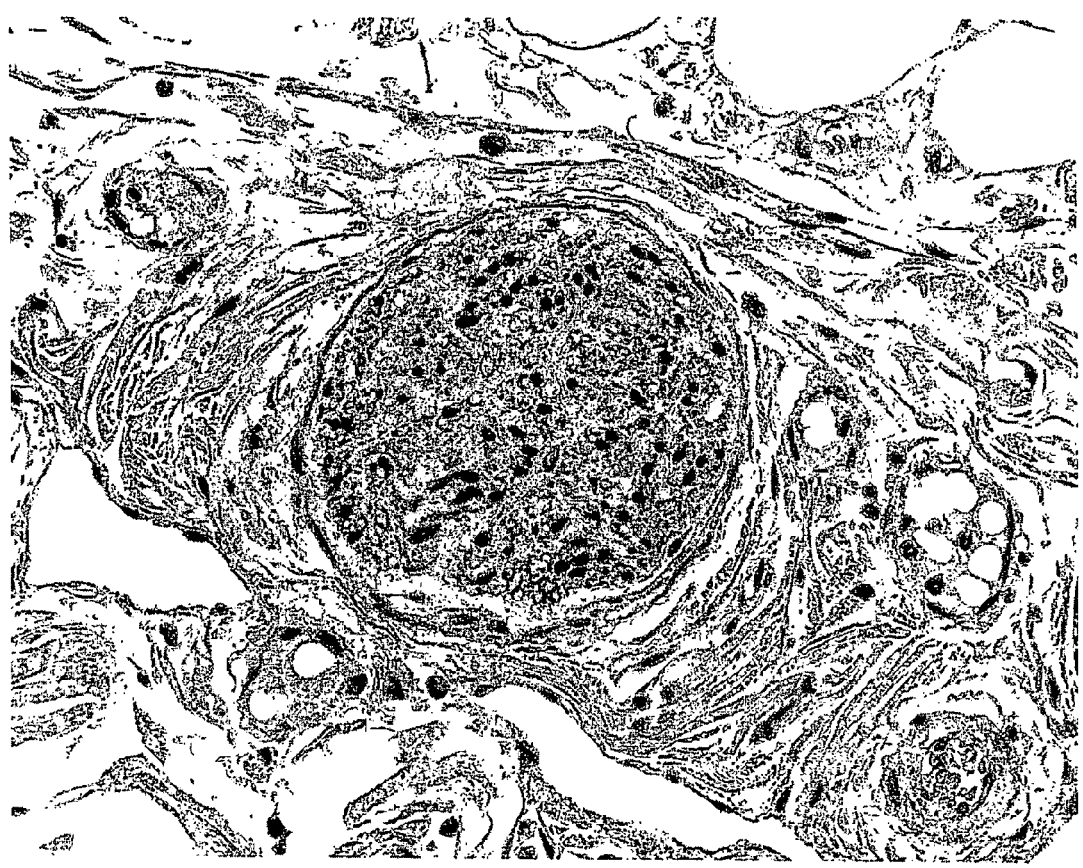

FIG. 6
Human nerve specimen (400×) processed using the standard procedure VIP300. Staining was performed using antibody: S-100 Code no. Z 311 lotno. 026 Dako. Ventana staining according to protocol
Specificity: nerves are stained and other structures are negative.
Intensity: diffuse intracytoplasmatic staining of the Schwann cells and the neurons. No background staining visible.

Figure 7:
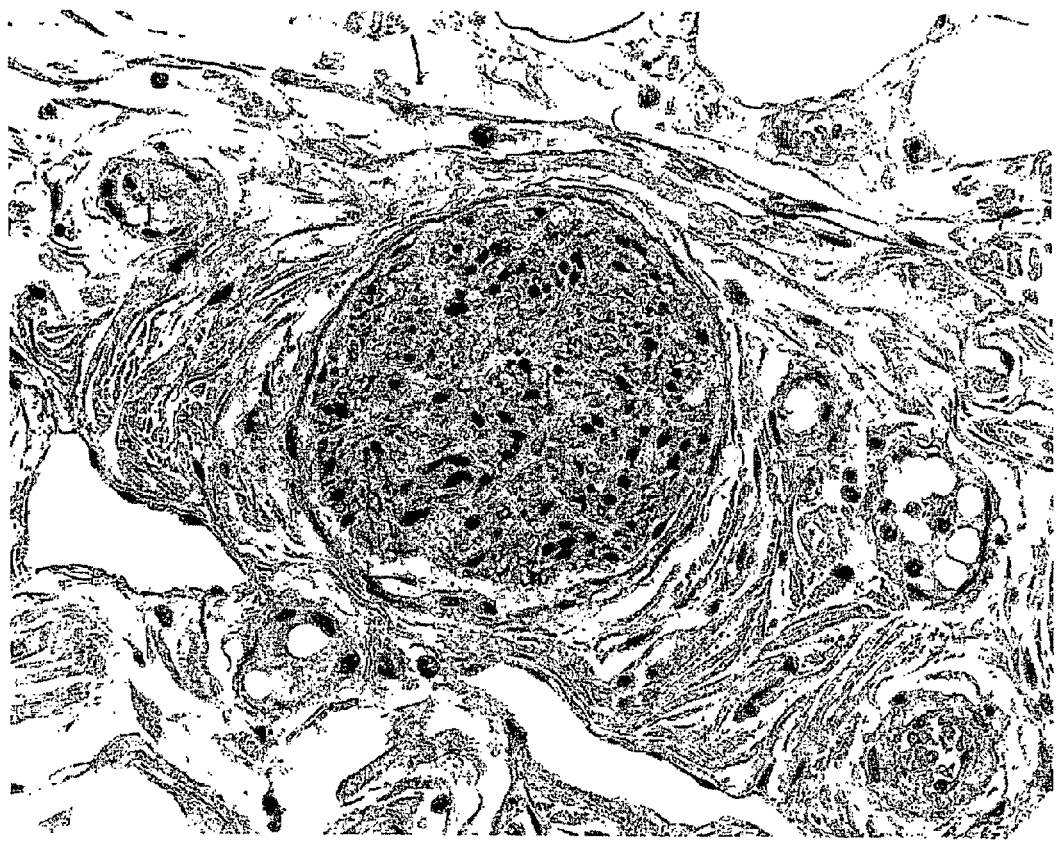

FIG. 7
Human nerve specimen (400×) of the same sample as shown in FIG. 6 but processed using supercritical carbon dioxide.
Staining was performed as described for FIG. 6.
Specificity: nerves are stained and other structures are negative.
Intensity: strong staining of the Schwann cells and the neurons. No background staining visible.

The invention claimed is:
1. A method for processing a biological sample for histological analysis, comprising the steps of:
 a) contacting the sample with a dehydrating agent;
 b) removing the dehydrating agent with a composition comprising a supercritical or a near supercritical fluid at a temperature in the range of 0.7 to 1.4 times its critical temperature and at a pressure in the range of 0.3 to 7 times its critical pressure; and c) replacing the supercritical fluid by infiltrating an embedding medium at a pressure of at least 1 bar.

2. A method according to claim 1, wherein said supercritical or near supercritical fluid is carbon dioxide.

3. A method according to claim 1, wherein said biological sample is a fresh, frozen, or fixed, or non-fixed tissue sample.

4. A method according to claim 1, wherein said biological sample comprises an organ or a part thereof.

5. A method according to claim 1, wherein said sample is dehydrated, defatted and/or decalcified prior to impregnation by using a composition comprising a supercritical fluid.

6. A method according to claim 5, wherein said composition additionally comprises a dehydrating agent.

7. A method according to claim 5, wherein said composition additionally comprises a decalcifying agent.

8. The method of claim 7, wherein the decalcifying agent is an acid.

9. The method of claim 1, wherein the embedding medium is paraffin.

10. The method of claim 3, wherein the biological specimen is a fresh, non-fixed sample.

11. The method of claim 6, wherein the dehydrating agent is an alcohol.

* * * * *

UNITED STATES PATENT AND TRADEMARK OFFICE
CERTIFICATE OF CORRECTION

PATENT NO. : 7,618,828 B2  Page 1 of 1
APPLICATION NO. : 10/562489
DATED : November 17, 2009
INVENTOR(S) : Bleuel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 802 days.

Signed and Sealed this

Twenty-sixth Day of October, 2010

David J. Kappos
*Director of the United States Patent and Trademark Office*